US007195781B2

(12) United States Patent
Miketin

(10) Patent No.: US 7,195,781 B2
(45) Date of Patent: Mar. 27, 2007

(54) METHOD FOR TREATMENT OF SKIN DISORDERS

(76) Inventor: Bronhilda Miketin, 2019 E. 2nd. St., Duluth, MN (US) 55816

( * ) Notice: Subject to any disclaimer, the term of this patent is extended or adjusted under 35 U.S.C. 154(b) by 441 days.

(21) Appl. No.: 10/896,475

(22) Filed: Jul. 13, 2004

(65) Prior Publication Data

US 2004/0253330 A1 Dec. 16, 2004

Related U.S. Application Data

(63) Continuation-in-part of application No. 10/419,517, filed on Apr. 21, 2003, now abandoned.

(51) Int. Cl.
A61K 35/12 (2006.01)
A61K 35/24 (2006.01)
A61K 36/00 (2006.01)
A61K 36/38 (2006.01)

(52) U.S. Cl. .................. 424/526; 424/520; 424/537; 424/725; 424/730; 424/771; 424/778; 514/861; 514/862; 514/863

(58) Field of Classification Search .................. None
See application file for complete search history.

(56) References Cited

U.S. PATENT DOCUMENTS

| 4,021,573 | A | 5/1977 | Lee .................. 424/318 |
| 5,104,877 | A | 4/1992 | Boger .................. 514/256 |
| 5,122,514 | A | 6/1992 | Boger et al. .................. 514/19 |
| 5,122,536 | A | 6/1992 | Perricone .................. 514/474 |
| 5,165,932 | A | 11/1992 | Horvath .................. 424/195.1 |
| 5,217,962 | A | 6/1993 | Burton et al. .................. 514/62 |
| 5,476,661 | A | 12/1995 | Pillai et al. .................. 424/401 |
| 5,616,324 | A | 4/1997 | Foster et al. .................. 424/195.1 |
| 5,747,064 | A | 5/1998 | Burnett et al. .................. 424/443 |
| 5,795,573 | A | 8/1998 | Paradise .................. 424/195.1 |
| 5,853,755 | A | 12/1998 | Foldvari .................. 424/450 |
| 5,962,010 | A | 10/1999 | Greff et al. .................. 424/443 |
| 6,153,208 | A * | 11/2000 | McAtee et al. .................. 424/402 |
| 6,316,001 | B1 | 11/2001 | Jaros et al. .................. 424/195.1 |
| 6,337,089 | B1 * | 1/2002 | Yoshioka et al. .................. 424/451 |
| 6,348,200 | B1 * | 2/2002 | Nakajima et al. .................. 424/401 |
| 6,379,715 | B2 | 4/2002 | Jaros et al. .................. 424/725 |
| 6,406,707 | B1 | 6/2002 | Jaros et al. .................. 424/401 |
| 2004/0208943 | A1 * | 10/2004 | Miketin .................. 424/730 |

FOREIGN PATENT DOCUMENTS

| EP | 0737480 A | 4/1996 |
| ES | 2186586 A | 5/2003 |
| GB | 2311009 A | 9/1997 |
| JP | 62230727 A | 10/1987 |
| JP | 04128219 A | 4/1992 |
| RU | 2127584 A | 3/1999 |
| WO | WO 91/15218 A | 10/1991 |

* cited by examiner

Primary Examiner—Christopher R. Tate
(74) Attorney, Agent, or Firm—Vidas, Arrett & Steinkraus, P.A.

(57) ABSTRACT

This invention relates to a method for the natural topical treatment of portions of skin of a person afflicted with a skin disorder such as dry skin, eczema, itchy skin, red skin, itchy eczema, inflamed skin, and/or cracked skin for the removal of itch and the restoration of the affected areas of skin to a normal condition. The natural treatment of a skin disorder initially involves formation of a natural ointment from the ingredients identified as lard; Marigold flowers; and pure beeswax. The natural ointment is formed by combination of the ingredients which includes heating. The ointment is then applied twice daily to affected areas of skin until a natural cure of the skin disorder is obtained. In addition, a therapeutic compress is applied to the affected skin. The compress may include Colts Foot Leaf, White Oak Bark, Burdock Root, Horsetail Herb, and water.

13 Claims, No Drawings

METHOD FOR TREATMENT OF SKIN DISORDERS

RELATED CASES

This application is a Continuation-In-Part patent application from patent application Ser. No. 10/419,517 filed Apr. 21, 2003 now abandoned, the entire contents of which is incorporated herein by reference in its entirety.

STATEMENT REGARDING FEDERALLY SPONSORED RESEARCH OR DEVELOPMENT (Not Applicable)

BACKGROUND OF THE INVENTION

The present invention relates to a method for the topical treatment of inflammation, rashes, hives, burns, psoriasis, hemorrhoids, poison ivy, insect stings, cuts, vitaligo, aging skin, and other types of undesirable skin disorders including but not necessarily limited to dry skin, eczema, itchy skin, red skin, itchy eczema, inflamed skin, and/or cracked skin. Skin disorders may generally be evidenced by the presence of skin elevations and scales which may be silvery in appearance. Psoriasis in general is a disease which accelerates the epidermal proliferation and proliferation of capillaries in the dermal region. In addition, psoriasis frequently results in the evasion of the dermis and epidermis by inflammation of the affected cells.

Areas of skin affected by psoriasis and other types of undesirable skin disorders also frequently lose water significantly faster than normal healthy skin. The areas of skin affected by skin disorders therefore tend to have increased metabolic rates, which in turn, causes a negative impact on tissue catabolism and potentially results in muscle wasting.

Skin disorders and Psoriasis, as a chronic skin disease, have been difficult to treat. Skin disorders may affect an individuals skin proximate to elbows, knees, trunk, and scalp. In the past, the treatment of skin disorders has included the use of various chemical agents such as dihydroxyanthralin, azarabine, colchicine, fluorouracil, methotrexate, methoxsalen, and the use of ultra-violet light. These methods have generally not provided satisfactory treatment of the skin disorder for individuals.

Alternatively, therapeutic regimes for the treatment of skin disorders have included the topical or intra-lesional application of corticosteroids, topical administration of anthralin or keratolytics, and the use of ultra-violet light on the affected areas. As is known in the art, no single therapy is ideal for the treatment of skin disorders and it is extremely rare for a patient to not receive treatment from several different therapeutic alternatives to attempt to prevent relapse and/or obtain remission for the skin disease or disorder. In addition, individuals frequently are required to be exposed to increased doses of medication which may magnify side effects adversely affecting the health of the individual.

Psoriasis is a relatively common skin disorder in which cell proliferation is increased up to 10 times the normal rate for an individual. The skin is the largest portion of the human body which is comprised of cells within three skin layers. Each of the skin layers is in a constant state of growth, with the outer layer being formed of predominantly dead tissue which is naturally being discarded at a normal rate. Replacement of cells from underlying layers is accomplished by cell division and maturation where cells move upwardly and outwardly at a rate which varies dependent upon the age, sex, and/or health of an individual. Skin disorders commonly cause an increased rate of turn over of cells within an affected area, which in turn increases the rate of cell growth and cell death. This increased rate of cell growth and cell death may result in injuries and/or disorders which accompany the increased synthesis of all tissue components, and further elevate the strain placed upon skin, other tissue, and/or the bio-synthetic capabilities of the cells within the affected area. The method and treatment of skin disorders as disclosed herein preferably slows cell proliferation and naturally treats areas of skin affected by one or more skin disorders. An individual's skin may then heal naturally, minimizing the risk of undesirable side effects and the relapse of the undesirable skin condition.

BRIEF DESCRIPTION OF THE INVENTION

This invention relates to a method for the natural topical treatment of portions of skin of a person afflicted with one or more types of skin disorders such as dry skin, eczema, itchy skin, red skin, itchy eczema, inflamed skin, and/or cracked skin, for the removal of itch and the restoration of the affected areas of skin to a normal condition. The natural treatment of one or more types of skin disorders initially involves the use of a natural topical ointment/salve and the then the use of a natural compress for application to the afflicted skin area. The natural ointment is generally formed of lard, dried Marigold flowers, and pure natural beeswax. The natural compress is generally formed from liquid which may include one or more boiled herbs such as Colts Foot Leaf, White Oak Bark, Burdock Root and Horsetail Herb. The consumption of natural Burdock Root or Nettles tea may be an additional preferred element of the method for the natural treatment of undesirable skin disorders.

Alternatively, the natural treatment of one or more types of skin disorders may involve formation of a natural ointment from the ingredients identified as lard, Marigold flowers, incense, Rosemary flower, Nettles extract, Marigold oil, St. Johns Wort oil, and pure beeswax. The natural ointment is formed by combination of the identified ingredients and the application of heat and stirring. The ointment is then applied twice daily to affected areas of skin until a natural cure of the undesirable skin condition is achieved.

It is a principal advantage of the present invention to provide a method for treatment of undesirable skin disorders formed of natural and inexpensive components which are safe and which fulfill the intended purpose of alleviation of symptoms of the undesirable skin disease, without fear of further injury to individuals.

Another principal advantage of the present invention is the provision of a method for treatment of undesirable skin disorders which includes a topical treatment completely formed of natural ingredients.

Still another principal advantage of the present invention is the provision of a method for treatment of skin disorders which reduces and/or eliminates "itchiness" of skin which is a common symptom/condition of a skin disorder.

Still another principal advantage of the present invention is the provision of a method for treatment of skin disorders which reduces and/or eliminates the undesirable "redness" or discoloration appearance of skin which is a common symptom of a skin condition.

Still another principal advantage of the present invention is the provision of a method for treatment of skin disorders which reduces and/or eliminates undesirable skin scales which is a common symptom/condition of a skin disorder.

Still another principal advantage of the present invention is the provision of a method for treatment of skin disorders which slows moisture loss of affected skin and tissue which is a common symptom/condition of skin disorders.

Still another principal advantage of the present invention is the provision of a method for treatment of skin disorders which facilitates healing of the individual layers of skin for return to a normal rate of growth.

Still another principal advantage of the present invention is the provision of a method for treatment of skin disorders which minimizes complications encountered by an individual exposed to topical and/or internal medication received during treatment of a skin disease.

Still another principal advantage of the present invention is the provision of a method for treatment of skin disorders which minimizes relapse or recurrence of the skin disease following completion of a treatment regime.

Still another principal advantage of the present invention is the provision of a method for treatment of skin disorders which naturally returns moisture to areas of skin affected with the undesirable skin disease.

Still another principal advantage of the present invention is the provision of a method for treatment of skin disorders which includes a topical ointment having lard.

Still another principal advantage of the present invention is the provision of a method for treatment of skin disorders which includes a topical ointment having Marigold flowers.

Still another principal advantage of the present invention is the provision of a method for treatment of skin disorders which includes a topical ointment having natural pure bee's wax.

Still another principal advantage of the present invention is the provision of a method for treatment of skin disorders which may include the consumption of Burdock Root or Nettles tea.

Still another principal advantage of the present invention is the provision of a method for treatment of skin disorders where the lard, Marigold flowers and pure beeswax, are boiled for a period of time of approximately 10 minutes, are removed from heat, are covered and are left for a period of 8 to 13 hours.

Still another principal advantage of the present invention is the provision of a method for treatment of skin disorders where the previously boiled mixture following cooling for 8 to 13 hours is melted and drained to provide a cream.

Still another principal advantage of the present invention is the provision of a method for treatment of skin disorders where the cooled cream is used as a natural topical ointment for the treatment of skin disorders by application into affected areas of skin at least once daily and preferably twice daily until such time as the symptoms for affected skin have improved.

Still another principal advantage of the present invention is the provision of a method for treatment of skin disorders where one or more herbs such as Colts Foot Leaf, White Oak Bark, Burdock Root and Horsetail Herb are combined with water and are soaked for a period of time of approximately 4–16 hours and then boiled, cooled, whereupon the solids are strained to yield a lukewarm liquid. The resulting liquid is then used to saturate a clean compress cloth such as cheesecloth to be placed directly into contact with an affected area of the skin.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The method for treatment of skin disorders such as dry skin, eczema, itchy skin, red skin, itchy eczema, inflamed skin, and/or cracked skin is disclosed herein. In general, the method for treatment of skin disorders involves the application of a topical ointment to an affected area of an individuals skin at least once per day and preferably twice per day for treatment of the undesirable skin condition.

The formulation of the ointment initiates with the acquisition of lard. The lard should be rinsed approximately 9 times in cold water prior to use in the formulation of the ointment described herein. Following rinsing, the lard should be drained. Approximately 4.5 kilograms, or 1 pound, of lard should be obtained and rinsed.

An individual should next obtain approximately 2.5 ounces to 4 ounces, or 70.9 to 113.4 grams, of dried full Marigold flowers for combination with the lard as described above.

It should be noted that other portions of the lard and full dried Marigold flowers may be used at the discretion of an individual provided that the ratio of the proportions is generally maintained for the formulation of the ointment described herein.

An individual will next obtain approximately 5 ounces, or 141.7 grams, of beeswax for combination with the lard and Marigold flowers. The beeswax is preferably pure.

The ingredients the lard, Marigold flowers, and pure beeswax are then heated to a boil and boiled for a period of time of approximately 5–10 minutes. Preferably the ingredients are heated within a clean porcelain and/or stainless steel utensil and are not heated within an aluminum utensil. The use of aluminum utensils may facilitate the burning and/or scalding of the mixture which is undesirable.

During the initial heating of the lard, full Marigold flowers, and pure beeswax, the mixture should be stirred every 30 seconds to 1 minute to reduce risk of burning during the initial heating step.

The stirring and heating of the mixture will result in the provision of a liquid mixture having a pale gold color. After the heat has been applied to the liquid mixture following boiling for a period 5–10 minutes, the heat should be terminated whereupon the mixture should be covered and allowed to stand for a period of time of 8–13 hours. The mixture should be brought to full boil within the above-identified 5–10 minute period of time, whereupon the heat may be terminated for covering for approximately 8–13 hours.

Following the period of time of 8–13 hours, heat may be reapplied to remelt the mixture. At such time as the mixture becomes re-melted, the mixture may be drained and/or strained. The draining of the mixture should occur through a clean fine tea filter which has not been previously utilized. The cream obtained following draining should be placed within new and clean containers which have been previously sterilized. A preferred type of container may be glass jars and/or plastic jars. Following placement of the cream ointment within the containers, a suitable device may be used to seal the containers to prevent future contamination.

The containers of the ointment are preferably refrigerated during storage prior to use by an individual. In the preferred embodiment no preservatives are added to the ointment to facilitate storage.

The ointment may be then extracted from the containers for application to an affected area of the skin for treatment of the undesirable skin condition.

Preferably, the affected area of skin is treated twice daily, once in the morning and once during the evening to facilitate healing. During use, the ointment is preferably rubbed and/or massaged into an affected area of skin. Itching is normally terminated within 2–3 weeks and normally 10 days following the initiation of treatment of the ointment disclosed herein. The topical ointment should be applied to the affected area of skin twice daily until the symptoms from the undesirable skin condition have ceased.

The affected areas of the skin treated with the ointment should not be exposed to soap, chemicals, or shampoo during the course of treatment. An individual may use a sensitive bar soap on non-affected areas of the body. The ointment applied to the affected areas of skin should be left on the skin all day and all night until such time as healing is achieved.

An individual using the ointment as described herein should avoid the consumption of caffeine and/or alcohol during treatment of an undesirable skin condition such as dry skin, eczema, itchy skin, red skin, itchy eczema, inflamed skin, and/or cracked skin.

Another sub-process for the method of treatment of skin as described herein involves the brewing of a liquid to be utilized as a compress for application to an affected area of skin, which has been previously treated with the ointment identified above. The brewing of the liquid to be used in association with the compress initiates with the acquisition of one or more herbs such as Colts Foot Leaf, White Oak Bark, Burdock Root and Horsetail Herb. Preferably, approximately 5 to 20 grams, and preferably 10 grams of Colts Foot Leaf; 5 to 20 grams, and preferably 10 grams of White Oak Bark; 5 to 20 grams, and preferably 10 grams of Burdock Root and approximately 5 to 100 grams, and preferably 10 grams, of Horsetail Herb. The Colts Foot Leaf, White Oak Bark, Burdock Root and Horsetail Herb should be placed into a pan whereupon approximately 1 liter of water is added. The mixture of Colts Foot Leaf, White Oak Bark, Burdock Root, Horsetail Herb, and water is then preferably left to soak for a period of time between 6 and 13 hours.

It should be noted that other portions of Colts Foot Leaf, White Oak Bark, Burdock Root and Horsetail Herb may be used at the discretion of an individual provided that the ratio of the proportions is generally maintained for the formulation of the liquid described herein.

The ingredients of the Colts Foot Leaf, White Oak Bark, Burdock Root, Horsetail Herb, and water, are then heated to a boil, and are boiled for a period of time of approximately 30 minutes. Preferably the ingredients are heated within a clean porcelain and/or stainless steel utensil and are not heated within an aluminum utensil. The use of aluminum utensils may facilitate the burning of the mixture which is undesirable.

During the initial heating of the Colts Foot Leaf, White Oak Bark, Burdock Root and Horsetail Herb, the liquid mixture should be stirred to reduce the risk of burning during the initial heating step.

Initially, the liquid mixture of water, Colts Foot Leaf, White Oak Bark, Burdock Root, and Horsetail Herb, may be brought to a high boil whereupon the application of heat may be reduced to boil the mixture at a low temperature for approximately ½ hour.

After the liquid mixture of Colts Foot Leaf, White Oak Bark, Burdock Root, Horsetail Herb, and water, has been boiled for approximately 30 minutes, the heat should be terminated whereupon the mixture should be allowed to stand for approximately 30 minutes. Following the cooling of the previously boiled Colts Foot Leaf, White Oak Bark, Burdock Root, Horsetail Herb, and water, and the cooling for approximately ½ hour, the liquid mixture may be strained through a strainer for extraction of the solids. The draining and/or straining of the mixture should occur through the use of a clean, fine tea filter which has not been previously utilized. The liquid obtained following draining should be placed within a new and clean container which has been previously sterilized. A preferred type of container may be a glass jar, plastic jar, and/or a bowl.

The container of the liquid may be stored at room temperature by an individual. In the preferred embodiment, no preservatives are added to the liquid to facilitate storage.

The liquid is preferably maintained at a lukewarm temperature for use in the treatment of skin disorders as described herein.

The liquid as obtained herein is preferably used to saturate a clean white cloth, such as cheesecloth, to be used as a compress to be placed over an affected area of skin. A compress saturated with the liquid as described herein is generally placed over an affected area of skin for a period of time of 1–3 hours. Following the application of the compress to an affected area of skin, the compress may be removed and discarded by an individual.

In addition to the use of the ointment and liquid compress as described herein, an individual may also facilitate treatment of the undesirable skin condition by drinking two cups of Burdock Root or Nettles tea each day, and preferably Burdock Root Tea, where one cup is consumed in the morning at least ½ hour prior to the consumption of food and one cup is consumed at night, every day during the course of treatment of the skin disorder.

The duration of treatment is generally dependent upon the length of time an individual has been inflicted with an undesirable skin condition. The treatment may be accomplished in a relatively short period of time of two to three weeks. Alternatively, in circumstances where an individual has previously suffered from an undesirable skin condition for an extended period of time, then the treatment may be required to extend over a two or three month period of time or extend for a duration of one year in severe conditions.

In addition to the procedures as identified above, an evening/night therapeutic clay may be applied to an afflicted area of the skin.

The therapeutic clay is similar to a cosmetic clay, pancake cover or paste mixture as applied to skin. The therapeutic clay is generally formed through the use of approximately 5 ounces, or 141 grams, of green clay powder, 1 example of which is French Green Clay Powder available from Frontier Natural Products Co-op of Norway, Iowa.

A sufficient volume of the brewed Colts Foot Leaf, White Oak Bark, Burdock Root/Horsetail Herb liquid identified above is added to the green clay powder and mixed within a clean bowl until the composition is soft. The softened mixed clay and liquid may then be used as a paste for application directly upon an afflicted area of the skin. The applied paste may then be covered with a clean white cloth such as a cheesecloth and held in position through the use of an elastic wrap such as an Ace® Bandage overnight. In the morning, the elastic wrap and cloth may be removed whereupon any dried clay may be brushed off from the afflicted area of the skin. The therapeutic ointment of lard, Marigold flowers, and beeswax as identified above may then be applied to the afflicted area of the skin as earlier described for all day treatment of the undesirable skin condition.

During treatment, healing skin treated with the ointment, compress, and therapeutic clay as described above, will initially assume a light brown color. As additional healing occurs, the color of the healing skin will change and clear to normal skin color for the individual.

In an alternative embodiment, the formulation of the ointment initiates with the acquisition of lard. The lard should be rinsed approximately 9 times in cold water prior to use in the formulation of the ointment described herein. Following rinsing, the lard should be drained. Approximately 0.5 kilograms of lard should be obtained and rinsed.

An individual should next obtain 2.5 ounces of full Marigold flowers for combination with the lard as described above.

It should be noted that other portions of lard and full Marigold flowers may be used at the discretion of an individual provided that the ratio of the proportions is generally maintained for the formulation of the ointment described herein.

An individual will next obtain approximately 100 grams of beeswax for combination to the lard and Marigold flowers. The beeswax is preferably pure.

An individual will next obtain at least 10 pieces of incense where each piece of incense is approximately the size of a kernal of corn for addition to the pure beeswax, Marigold flowers and lard. More than 10 pieces of incense may be used at the discretion of an individual. The size of the incense may exceed the average size of a kernel of corn and relatively large portions of incense may be used as a portion of the treatment formulation.

An individual will next obtain at least three strips of Rosemary flower for addition to the pure beeswax, Marigold flowers, lard, and incense. Again, it should be noted that the amount of the individual ingredients may vary at the discretion of an individual provided that a ratio of proportions of the identified ingredients is generally maintained.

The ingredients of the lard, Marigold flowers, pure beeswax, incense, and Rosemary flower are then heated to boil and boiled for a period of approximately 5 to 10 minutes. Preferably the ingredients are heated within a clean porcelain and/or stainless steel utensil and are not heated within an aluminum utensil. The use of aluminum utensils may facilitate the burning of the mixture which is undesirable.

During the initial heating of the lard, full Marigold flowers, pure beeswax, incense, and strings of Rosemary flower, the mixture should be stirred every 30 seconds to 1 minute to reduce risk of burning during the initial heating step.

The stirring and heating of the mixture will result in the provision of a liquid mixture having a pale gold color. After the heat has been applied to the liquid mixture following boiling for a period of 5 to 10 minutes, the heat should be terminated whereupon the mixture should be covered and allowed to stand for 8 to 10 hours. The mixture should be brought to full boil within the 5 to 10 minute period of time whereupon heat may be terminated for covering for 8 to 10 hours.

Following a period of time of 8 to 10 hours, heat may be reapplied to melt the mixture. At such time as the mixture becomes melted, the mixture may be drained whereupon two ounces of Nettles extract should be added to the mixture in conjunction with two ounces of St. Johns Wort oil and two ounces of Marigold oil. The mixture including the two ounces of Nettles extract and the two ounces of St. Johns Wort oil and two ounces of Marigold oil should then be mixed whereupon draining may occur. The draining of the mixture should occur through a clean fine tea filter which has not been previously utilized. The cream obtained following draining should be placed within new and clean containers which have previously been sterilized. A preferred type of container may be glass jars and/or plastic jars. Following placement of the cream ointment within the containers, a suitable device may be used to seal the containers to prevent future contamination.

The containers of the ointment may be stored at room temperature or refrigerated at the discretion of an individual. In the preferred embodiment no preservatives are added to the ointment to facilitate storage.

The ointment may be then extracted from the containers for application to an affected area of skin for the treatment of the undesirable skin condition. Preferably the affected area of skin is treated twice daily, once in the morning and once during the evening to facilitate healing. During use, the ointment is preferably rubbed and/or massaged into an affected area of skin. Itching is normally terminated within two to three weeks and normally 10 days following the initiation of treatment of the ointment disclosed herein. The topical ointment should be applied to the affected area of skin twice daily until the undesirable skin condition has been cured.

The affected areas of skin treated with the ointment should not be exposed to soap, chemicals, or shampoo during the course of treatment. An individual may use a sensitive bar soap on non-affected areas of the body. The ointment applied to the affected areas of skin should be left on the skin all day and all night until such time as healing is achieved.

An individual using the ointment as described herein should avoid the consumption of caffeine and/or alcohol during treatment of an undesirable skin condition such as dry skin, eczema, itchy skin, red skin, itchy eczema, inflamed skin, and/or cracked skin.

In addition to the use of the ointment as described herein, an individual may also facilitate treatment of the undesirable skin condition by drinking two cups of Nettles tea where one cup is consumed in the morning and one cup is consumed at night each and every day during the course of treatment.

The duration of treatment is generally dependent upon the length of time an individual has been inflicted with an undesirable skin condition. The treatment may be accomplished in a relatively short period of time of two to three weeks. Alternatively, in circumstances where an individual has previously suffered from an undesirable skin condition for 20 to 30 years, then treatment may be required to extend over a two or three month period of time.

During treatment, healing skin treated with the natural ointment described herein will initially assume a light brown color. As additional healing occurs, the color of the healing skin will change and clear to the normal skin color for the individual.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for topically treating a skin condition selected from the group consisting of inflammation, rashes, hives, burns, psoriasis, vitaglio, hemorrhoids, poison ivy, insect stings, cuts, aging skin, dry skin, eczema, itchy skin, red skin, inflamed skin, and cracked skin, said method comprising:
   a) application of a topical ointment upon said skin condition at least once per day for a period of at least 7 days, said topical ointment comprising a mixture of approximately 64% lard, 16% Marigold flowers, and 20% beeswax; and
   b) application of a compress upon said skin condition at least once per day for a period of at least 7 days, said compress comprising a therapeutic liquid and a liquid retainer, said therapeutic liquid comprising Burdock Root, Horsetail Herb, and water.

2. The method according to claim 1, said therapeutic liquid comprising Colts Foot Leaf and White Oak Bark.

3. The method according to claim 1, said liquid retainer further comprising therapeutic clay.

4. The method according to claim 1, whereby the mixture is prepared by a process comprising boiling said lard, said Marigold flowers, and said beeswax for at least 5 minutes to form said mixture and allowing said mixture to cool for at least 6 hours, prior to the application of said mixture.

5. The method according to claim 4, the process further comprising reheating said mixture following said cooling and straining said mixture.

6. The method according to claim 1, whereby the mixture is prepared by a process comprising the steps of:
   adding said Burdock Root, said Horsetail Herb, and said water into a mixing vessel in a proportionate amount of approximately 10 grams of said Burdock Root, 10 Grams of said Horsetail Herb, and 1 liter of water;
   applying heat to said mixing vessel to boil said Burdock Root, said Horsetail Herb, and said water for a period of approximately 30 minutes;
   allowing said boiled Burdock Root, said boiled Horsetail Herb, and said boiled water to cool for approximately 30 minutes; and
   straining said cooled Burdock Root, Horsetail Herb, and water to obtain said therapeutic liquid, prior to the application of said mixture.

7. The method of claim 1, said liquid retainer comprising a cloth.

8. The method according to claim 7, whereby the therapeutic liquid saturates the liquid retainer.

9. The method according to claim 8, said liquid retainer further comprises a therapeutic clay.

10. The method according to claim 9, whereby said therapeutic clay is prepared by a process comprising the steps of:
    adding a portion of clay to a mixing vessel; and
    mixing said clay with said therapeutic liquid to provide said therapeutic clay.

11. The method according to claim 1, further comprising the step of consuming at least one cup of Burdock Root tea each day for said period of 7 days.

12. The method according to claim 3, further comprising the step of consuming at least one cup of Burdock Root tea each day for said period of 7 days.

13. The method according to claim 12, whereby at least two cups of Burdock Root tea are consumed each day for said period of 7 days.

* * * * *